United States Patent [19]
Chafetz et al.

[11] 4,325,876
[45] Apr. 20, 1982

[54] PROCESS FOR THE MANUFACTURE OF AN ALKENYLSUCCINIC ANHYDRIDE

[75] Inventors: Harry Chafetz, Poughkeepsie, N.Y.; Gary D. Lee, Spring, Tex.

[73] Assignee: Texaco Inc., White Plains, N.Y.

[21] Appl. No.: 221,179

[22] Filed: Dec. 29, 1980

[51] Int. Cl.³ .......................................... C07D 307/60
[52] U.S. Cl. ................................................ 260/346.74
[58] Field of Search ................................... 260/346.74

[56] References Cited

U.S. PATENT DOCUMENTS

| | | | |
|---|---|---|---|
| 3,231,587 | 1/1966 | Rense | 260/346.74 |
| 3,409,638 | 11/1968 | Selwitz | 260/346.74 |
| 3,927,041 | 12/1975 | Cengel et al. | 260/346.74 |

*Primary Examiner*—Richard Raymond
*Attorney, Agent, or Firm*—Carl G. Ries; Robert A. Kulason; James J. O'Loughlin

[57] ABSTRACT

A method for producing an alkenylsuccinic anhydride by reacting a mixture of an olefin polymer with maleic anhydride, the improvement which comprises reacting said reaction mixture at a temperature in the range of 100° to 300° C. while contacting said mixture with an oxygen-containing gas during said reaction.

9 Claims, No Drawings

PROCESS FOR THE MANUFACTURE OF AN ALKENYLSUCCINIC ANHYDRIDE

BACKGROUND OF THE INVENTION

1. Field of the Invention

This invention is directed to an improved method for preparing alkenyl-substituted succinic anhydrides.

Alkenyl-substituted succinic anhydrides are valuable intermediates for the production of products which have a wide range of uses. For example, the acids and the anhydrides are useful as rust inhibiting agents in mineral and synthetic lubricating oils and in paint and other protective coating compositions. The reaction products of alkenylsuccinic anhydrides with amines results in the production of alkenyl-substituted succinamic acids and succinimides and provides products which have valuable friction modifying and detergent-dispersant properties for lubricating oil compositions.

The alkenylation of maleic anhydride to produce an alkenyl-substituted succinic anhydride particularly with the higher molecular weight olefin polymers is a relatively slow, inefficient process. The art describes many processes for improving the reaction between an olefin polymer and maleic anhydride. One such process involves halogenating the olefin polymer prior to reacting with it maleic anhydride. Many processes for improving this reaction are based on the use of a catalyst promoter. Thus, processes have been proposed which involve the use of a halogenated organic or inorganic catalyst such as a chlorinated or brominated organic or inorganic compound. Another type of promoted process involves the use of a free radical initiator in the process.

2. Description of the Prior Art

U.S. Pat. No. 3,231,587 discloses a process for reacting an aliphatic polymer of a lower metal olefin and maleic anhydride by contacting the reactants at a temperature of above about 140° C. in the presence of about 1 mole of chlorine for each mole of maleic anhydride.

U.S. Pat. No. 3,927,041 discloses a method for preparing an alkenylsuccinic anhydride by reacting a viscous polybutene with an unsaturated aliphatic dicarboxylic acid anhydride in the presence of 1,3-dibromo-5,5-dialkyl-substituted hydantoin.

SUMMARY OF THE INVENTION

In accordance with this process, an improved method for preparing an alkenyl-substituted succinic anhydride is provided which comprises reacting a mixture of an olefin polymer and maleic anhydride at a temperature ranging from about 100° to 300° C. in the presence of or in contact with an oxygen-containing gas. In a preferred embodiment of this process, an olefin polymer having an average molecular weight from about 300 to 3500 is reacted with maleic anhydride in contact with air as the oxygen-containing gas.

SPECIFIC EMBODIMENTS OF THE INVENTION

The present invention relates to a method for reacting maleic anhydride with a polyolefin to produce an alkenyl-substituted succinic anhydride. This reaction may be conducted between maleic anhydride and an olefin polymer derived from the polymerization of an olefinic hydrocarbon having from 2 to 5 carbon atoms by means of conventional polymerization processes to produce an olefin polymer having an average molecular weight ranging from about 300 to 3500. In a preferred aspect of the invention, the olefin polymer will have an average molecular weight ranging from about 800 to 2000. More particularly, valuable dispersants for lubricating oil compositions can be produced from alkenyl-substituted succinic anhydrides prepared according to the process of the invention when the alkenyl radical is derived from the polyolefin having from about 1000 to 1500 molecular weight.

A variety of olefin polymers and copolymers having the prescribed average molecular weight can be employed in the process of the invention. Examples of suitable polymers include polyethylene, polypropylene, ethylene-propylene copolymers, polyisobutylene, polybutene-1 and poly-butene-2.

This reaction is generally conducted at a temperature ranging from about 100° to 300° C. It is preferred, however, to use reaction temperatures ranging from about 150° to 260° C. with a particularly preferred reaction temperature ranging from about 180° to 225° C.

The critical feature of the present process is the use of an oxygen-containing gas for promoting the reaction between maleic anhydride and the polyolefin. A gaseous mixture in which oxygen is the only active component can be employed in the process of the invention. In general, the gaseous mixture may consist of from 10 to 50 volume % of oxygen in combination with an inert gas such as nitrogen. Air is particularly preferred as the oxygen-containing gas for this process.

In general, the maleic anhydride and polyolefin polymer reactants are admixed in a closed reactor which can maintain the required reaction temperature as well as provide adequate contact by means of mixing or other agitation with the oxygen-containing gas promoter of this process. This may be accomplished by a simple sweep of the oxygen-containing gas through the reactor or more intimate contact can be achieved by bubbling the oxygen-containing gas through the heated reaction mixture.

The mole ratio of the reactants is not critical. In general, the maleic anhydride and polyolefin are reacted at a mole ratio in the range from about 0.5 to 2.0 moles of maleic anhydride per mole of the polyolefin reactant.

The following examples illustrate the practice of this invention.

EXAMPLE I

Two hundred grams of polyisobutylene having an average molecular weight of about 1300 (Indopol H-300) and 30 grams of maleic anhydride were put into a reactor equipped with a stirrer, reflux condenser and a gas inlet tube designed to provide a gas sweep of the reaction mixture. The reaction mixture was heated to 150° C. and maintained at this temperature for 10 hours while nitrogen gas was passed into the reaction vessel in contact with the reactants at a flow rate of about 100 mls. of nitrogen per minute. At the end of the reaction period, unreacted maleic anhydride was removed by stripping at about 140° C., under 4 mm mercury pressure. The product was dissolved in 300 mls. of n-heptane, filtered through filter aid and the solids removed under reduced pressure. An analysis of the product both for its Saponification No. and for the percent conversion of the polyisobutylene by a modified ASTM D-2548 procedure showed it to have a Saponification No. of 3.5 and polyisobutylene conversion 5.5%.

EXAMPLE II

The procedure employed in this example was similar to Example I except that air was pumped into the reaction vessel in contact with the hot reaction mixture rather than nitrogen at the same gas flow rate. On analysis, the product was found to have a Saponification No. of 21 and a polyisobutylene conversion of 44%.

EXAMPLE III

This example was conducted similarly to Example II except that a glass fitted sparger was used on the gas inlet tube in the vessel in order to introduce and disperse the air directly into the reaction mixture. Analysis of the product found it to have a Saponification No. of 21 and a polyisobutylene conversion of 43%.

EXAMPLE IV

Two hundred grams of polyisobutylene having an average molecular weight of about 1300 and 30 grams of maleic anhydride were reacted in contact with a nitrogen gas sweep similar to the procedure used in Example I above except that the reaction was conducted at 200° C. for a reaction period of about 5 hours. An analysis of the product produced in this reaction showed that it had a Saponification No. of 32 and polyisobutylene conversion of 40%.

EXAMPLE V

This example was conducted in a manner similar to Example IV above except that air was employed as the gas sweep instead of nitrogen.

Analysis of the product of this example showed that it had a Saponification No. of 43 and a polyisobutylene conversion of 52%.

The results of the foregoing runs are summarized in the following table.

TABLE I
POLYISOBUTYLENE (1300 MW) MALEIC ANHYDRIDE REACTION

| Example | Reaction Conditions | Sap. No. | Polyisobutylene Conversion |
|---|---|---|---|
| I | Nitrogen sweep, 150° C., 10 hours | 2.5 | 5.5 |
| II | Air sweep, 150° C., 10 hours | 21 | 44 |
| III | Air via sparging at 150° C., 10 hours | 21 | 43 |
| IV | Nitrogen sweep, 200° C., 5 hours | 32 | 40 |
| V | Air Sweep, 200° C., 5 hours | 43 | 52 |

The polyisobutylene (1300 MW) succinic anhydrides prepared in the above examples were reacted with ethylenediamine according to conventional methods to produce a nitrogen-containing dispersant, namely an N-aminoethylpolyisobutenyl (1300 MW) succinimide. The nitrogen-containing dispersants prepared from the polyisobuteneyl (1300 MW) succinic anhydrides prepared in accordance with the air-promoted process of the invention, namely Examples II, III and IV, were outstandingly effective as dispersants for lubricating oil compositions when tested in the Bench VC Dispersancy Test.

We claim:

1. In a process for thermally reacting a reaction mixture of a polyolefin having an average molecular weight ranging from about 300 to 3500 with maleic anhydride to form an alkenyl-substituted succinic anhydride, the improvement which comprises effecting said reaction in the absence of a halogenated compound at a temperature ranging from about 100° to 300° C. while contacting said reaction mixture with oxygen-containing gas.

2. A process according to claim 1 in which said reaction is conducted at a temperature ranging from about 150° to 260° C.

3. A process according to claim 1 in which said reaction is conducted in the presence of air as the oxygen-containing gas.

4. A process according to claim 1 in which said polyolefin is polyisobutylene having an average molecular weight ranging from about 800 to 2000.

5. A process according to claim 1 in which said oxygen-containing gas contains from 10 to 50 volume percent of oxygen.

6. A process according to claim 1 in which the mole ratio employed is from about 0.5 to 2.0 moles of said maleic anhydride per mole of said polyolefin.

7. A process for thermally reacting a reaction mixture of a polyisobutylene having an average molecular weight ranging from about 800 to 2000 with maleic anhydride to form a polyisobutenyl-substituted succinic anhydride, the improvement which comprises effecting said reaction in the absence of a halogenated compound at a temperature ranging from about 150° to 260° C. while contacting said reaction mixture with an oxygen-containing gas.

8. A process according to claim 7 in which said reaction is conducted in the presence of air.

9. A process according to claim 7 in which the mole ratio is from about 0.5 to 2.0 moles of said maleic anhydride per mole of said polyisobutylene.

* * * * *